(12) United States Patent
Gatturna et al.

(10) Patent No.: US 10,531,863 B2
(45) Date of Patent: Jan. 14, 2020

(54) QUICK DISCONNECT ASSEMBLY AND METHOD OF USE

(71) Applicant: Smith & Nephew, Inc., Memphis, TN (US)

(72) Inventors: Roland F. Gatturna, Bourne, MA (US); Stephen A. Santangelo, Sturbridge, MA (US)

(73) Assignee: Smith & Nephew, Inc., Memphis, TN (US)

( * ) Notice: Subject to any disclaimer, the term of this patent is extended or adjusted under 35 U.S.C. 154(b) by 412 days.

(21) Appl. No.: 15/542,251

(22) PCT Filed: Jan. 8, 2016

(86) PCT No.: PCT/US2016/012572
§ 371 (c)(1),
(2) Date: Jul. 7, 2017

(87) PCT Pub. No.: WO2016/112244
PCT Pub. Date: Jul. 14, 2016

(65) Prior Publication Data
US 2018/0263609 A1 Sep. 20, 2018

Related U.S. Application Data

(60) Provisional application No. 62/101,161, filed on Jan. 8, 2015.

(51) Int. Cl.
*A61B 17/04* (2006.01)
*A61B 17/00* (2006.01)
*B25G 3/12* (2006.01)

(52) U.S. Cl.
CPC ............. *A61B 17/00* (2013.01); *A61B 17/04* (2013.01); *A61B 2017/0046* (2013.01); *B25G 3/12* (2013.01)

(58) Field of Classification Search
CPC . A61B 17/00; A61B 17/04; A61B 2017/0046; B25G 3/04; B25G 3/12;
(Continued)

(56) References Cited

U.S. PATENT DOCUMENTS 3,585,824 A    6/1971   Schenk
4,143,446 A * 3/1979   Down ..................... F16G 11/06
                                                                                      24/115 R
(Continued)

OTHER PUBLICATIONS

Chinese Application No. 2016800052874 the First Office Action.
(Continued)

*Primary Examiner* — Matthieu F Setliff
(74) *Attorney, Agent, or Firm* — Burns & Levinson, LLP; Joseph M. Maraia (57) ABSTRACT

A quick disconnect assembly including a tubular housing. The housing includes a cam pin secured to the housing and a nut positioned within the housing cannulation. The nut has a first threaded channel adapted to engage a threaded shaft, a second, non-threaded channel extending at an angle to the first channel, and an arcuate groove formed on an outer surface of the nut. When the cam pin of the housing engages the groove at about a distal end of the nut, the nut is positioned in a loading position where the second channel extends approximately parallel to the longitudinal axis of the housing. When the cam pin engages the groove at about a proximal end of the nut, the nut is positioned in a locking position where the first channel extends approximately parallel to the longitudinal axis of the housing.

13 Claims, 6 Drawing Sheets

(58) Field of Classification Search
CPC .... B25G 3/16; B25G 3/20; B25G 3/22; Y10T 16/469; Y10T 24/3936; Y10T 24/394
USPC ........................................ 403/DIG. 3, DIG. 4
See application file for complete search history.

(56) References Cited

U.S. PATENT DOCUMENTS

| | | | | |
|---|---|---|---|---|
| 4,247,163 | A * | 1/1981 | Lumpp | G02B 6/3855 24/115 G |
| 4,597,699 | A | 7/1986 | Ramunas | |
| 4,941,246 | A * | 7/1990 | Finnegan | B23D 71/04 16/422 |
| 5,125,761 | A * | 6/1992 | Cullen | E04H 9/02 24/132 R |
| 5,344,194 | A | 9/1994 | Hatagishi et al. | |
| 6,283,966 | B1 * | 9/2001 | Houfburg | A61B 17/1757 606/279 |
| 6,461,075 | B2 * | 10/2002 | Bickel | B25G 3/28 15/145 |
| 6,605,077 | B2 * | 8/2003 | Whittier | A61B 10/06 606/1 |
| 6,659,997 | B1 * | 12/2003 | Casutt | A61B 17/8875 16/422 |
| 6,669,702 | B2 * | 12/2003 | Lechot | A61B 17/88 279/103 |
| 6,862,776 | B2 * | 3/2005 | Chen | F16B 7/1463 16/113.1 |
| 6,874,201 | B2 * | 4/2005 | Ta | B05C 17/0205 16/427 |
| 7,587,791 | B2 * | 9/2009 | Liou | B25B 23/0035 16/422 |
| 7,721,391 | B2 * | 5/2010 | Bukovitz | B25G 3/14 15/145 |
| 8,800,113 | B1 * | 8/2014 | Charvet | B25G 3/18 16/422 |
| 2003/0001387 | A1 | 1/2003 | Tawara et al. | |
| 2003/0085572 | A1 | 5/2003 | Froment et al. | |
| 2005/0121906 | A1 | 6/2005 | Tiberghien et al. | |

OTHER PUBLICATIONS

Chinese Application No. 2016800052874 Search Report.
International Search Report for PCT/US16/012572 dated Jun. 14, 2016.
European Application No. 16703637.5-1122 Examination Report dated Oct. 16, 2019.

* cited by examiner

QUICK DISCONNECT ASSEMBLY AND METHOD OF USE

CROSS-REFERENCE TO RELATED APPLICATIONS

This application is the U.S. national phase entry under 35 U.S.C. § 371 of International Application No. PCT/US2016/012572, filed Jan. 8, 2016, entitled QUICK DISCONNECT ASSEMBLY AND METHOD OF USE, which in turn claims priority to and benefit of U.S. Provisional Application No. 62/101,161, filed Jan. 8, 2015, the contents of which are incorporated herein by reference in their entirety for all purposes.

FIELD OF THE INVENTION

The present disclosure relates to quick disconnect assemblies in general and, more particularly, to a quick disconnect housing and shaft assembly used in a surgical apparatus.

BACKGROUND

A surgical apparatus may contain a shaft inserted into a housing and secured in place in many ways, such as with a set screw, a locking shaft collar, or a cross-pin fitting into a groove. During a surgical operation, the shaft may need to be detached and removed from the housing, for example, with a surgical apparatus that has a reusable handle and a single-use front end. Therefore, it is desirable for the surgical apparatus to have a quick disconnect mechanism between the housing and shaft that is simple, cost-effective, reliable and easy to use.

SUMMARY

The disclosure described herein is a quick disconnect assembly including a generally tubular housing extending between distal and proximal ends, and a rotatable nut adapted to secure a threaded shaft. This mechanism can be applied to any surgical construct where a removable component is desired, particularly with reusable and disposable components. Advantageously, the quick disconnect assembly of this disclosure will accommodate a variety of shaft lengths and/or configurations. Furthermore, the quick disconnect assembly of this disclosure provides the ability to slide and lock with a separate axial movement. Both the shaft and the housing can easily be assembled and disassembled repeatedly. The housing and shaft can further be assembled and disassembled at adjustable positions. The adjustments to the positions can be of any granularity.

The quick disconnect assembly of this disclosure is furthermore advantageous over the prior art because current apparatuses require at least one additional mechanical element to lock the shaft to the nut. The present disclosure uses fewer parts, leading to simplicity, reduced costs, and ease of use for surgeons.

In an embodiment of the quick disconnect assembly of this disclosure, the quick disconnect assembly includes a tubular housing extending along a longitudinal axis between a proximal end and a distal end. The housing includes a cannulation extending between the proximal and distal ends. The cannulation includes a first portion extending from the housing proximal end and a second portion. The second portion is continuous with the first portion, extending from the housing distal end and having a diameter smaller than the first portion.

The housing further includes a cam pin secured to the housing and extending transverse to the longitudinal axis within the first portion. The housing also includes a nut positioned within the housing. The nut includes a first, threaded channel formed through a length of the nut and adapted to threadingly engage a threaded shaft, a second, non-threaded channel extending at a selected angle with respect to the first channel and intersecting the first channel, the second channel having a diameter greater than the threaded shaft, and an arcuate groove formed on an outer surface of the nut and extending between the proximal and distal ends of the nut. The first channel of the nut is oriented such that, when the cam pin engages the groove at about a distal end of the nut, the nut is positioned in a loading position where the second channel extends approximately parallel to the longitudinal axis of the housing. The second channel of the nut is oriented such that, when the cam pin engages the groove at about a proximal end of the nut, the nut is positioned in a locking position where the first channel extends approximately parallel to the longitudinal axis of the housing.

In further embodiments, the housing is tubular. The nut comprises a non-threaded channel. The quick disconnect assembly comprises a threaded shaft threadingly engaged with the first channel of the nut and a nut carrier axially coupled to the nut. Distal advancement of the threaded shaft while the nut is in the loading position engages a distal end of the threaded shaft with a nut carrier and distally advances the nut carrier and nut. The nut is urged from the loading position to the locking position by the distal advancement of the threaded shaft such that threads of the first channel threadingly engage the threads of the threaded shaft. Insertion of the threaded shaft into the nut is not inhibited by the second channel when the nut is in the loading position. The diameter of the second portion of the housing cannulation is selected to prevent distal movement of the nut when the nut is in the locking position. A diameter of the non-threaded channel of the nut is selected to allow passage of the threaded shaft. A clearance inside the housing is selected to allow the nut to rotate into the loading position but to restrict the nut from rotating into a position that would disengage the threaded shaft from the first channel of the nut.

In an embodiment of the method of connecting a housing and shaft of this disclosure, the method includes: engaging a cam pin secured to a housing with a distal end of a groove formed in the surface of a nut, the nut comprising a first channel in communication with a second channel extending at a selected angle with respect to the first channel and intersecting the first channel, wherein the nut is positioned within a cannulation of the housing such that the second channel of the nut extends approximately parallel to a longitudinal axis of the housing; inserting a threaded shaft into the first channel of the nut; and distally advancing the threaded shaft within the nut until a distal end of the threaded shaft engages with a nut carrier and distally advances the nut carrier and the nut within the cannulation of the housing. The distal advancement of the nut within the cannulation of the housing causes the cam pin to move from the distal end of the groove to the proximal end of the groove. When the cam pin engages the proximal end of the groove, the first channel of the nut extends approximately parallel to the longitudinal axis of the housing and the threaded shaft is lockingly engaged with the threaded channel of the nut. The cannulation of the housing comprises a first portion and a second portion, a diameter of the second portion being smaller than a diameter of the first portion. The diameter of the second portion of the housing cannulation is selected to prevent distal movement of the nut when the threaded shaft is lockingly engaged with the threaded channel of the nut.

BRIEF DESCRIPTION OF THE DRAWINGS

The foregoing will be apparent from the following more particular description of example embodiments of the disclosure, as illustrated in the accompanying drawings.

DETAILED DESCRIPTION

Examples of the quick disconnect assembly of this disclosure will now be discussed with reference to the figures.

In the description that follows, like components have been given the same reference numerals, regardless of whether they are shown in different examples. To illustrate example (s) in a clear and concise manner, the drawings may not necessarily be to scale and certain features may be shown in somewhat schematic form. Features that are described and/or illustrated with respect to one example may be used in the same way or in a similar way in one or more other examples and/or in combination with or instead of the features of the other examples.

Comprise, include, and/or plural forms of each are open ended and include the listed parts and can include additional parts that are not listed. And/or is open ended and includes one or more of the listed parts and combinations of the listed parts.

FIGS. 1A-E illustrate an example embodiment of the quick disconnect assembly 100 of this disclosure and its method of use. The components of the quick disconnect assembly 100 may vary in size, shape or materials and are selected to be suitable to the surgical apparatus of their use.

Figure 1A:
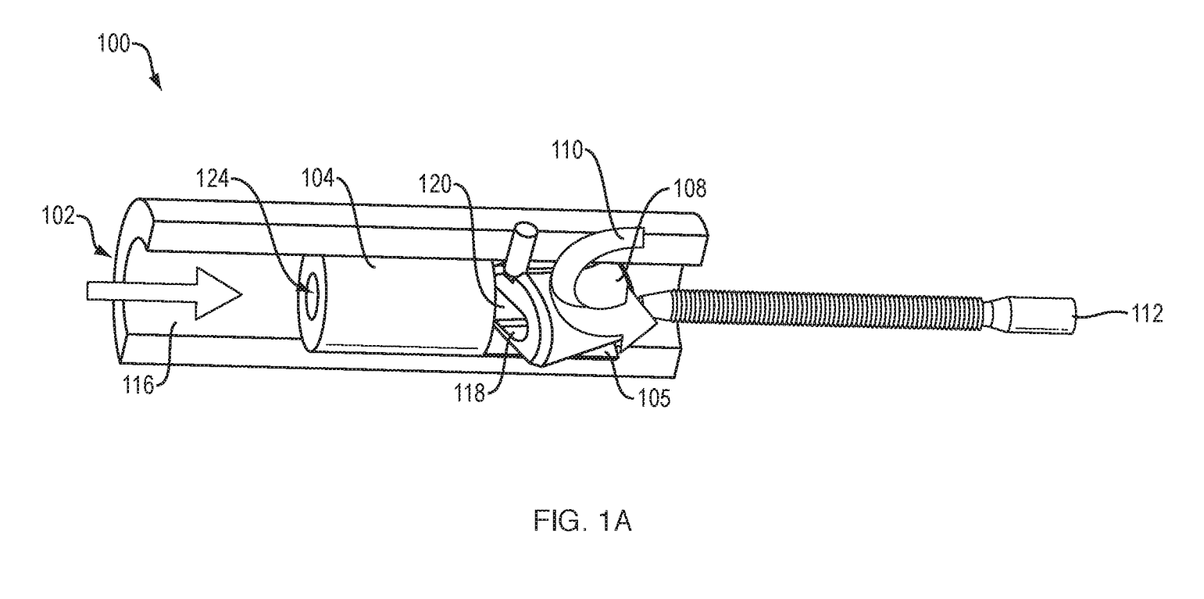
FIG. 1A is a diagram illustrating an example embodiment of the loading position of present disclosure.

In FIG. 1A, the quick disconnect assembly 100 generally includes a housing 102 (shown in cross-section), a nut carrier 104, a rotatable nut 108 and a threaded shaft 112. The nut carrier 104 includes a distally extending bed 105 on which the rotatable nut 108 rests. The housing 102 can be a tubular housing extending along a longitudinal axis between a proximal end and a distal end. However, a person of ordinary skill in the art can recognize that the housing 102 can be extrapolated as a housing of another shape in other embodiments. The housing 102 can include a cannulation 116 extending between the proximal and distal ends. The nut carrier 104 and the rotatable nut 108 are positioned within the cannulation 116, as described in more detail below. The nut carrier 104 includes an internal, non-threaded cannulation 124 extending from a proximal to a distal end. The shapes of both of the nut carrier 104 and the rotatable nut 108 can be tubular, but are selected to match the inside shape of the cannulation 116. The threaded shaft 112 may be disposable. The rotatable nut 108 includes a first channel 118 and a second channel 120, described in more detail below.

Figure 1B:
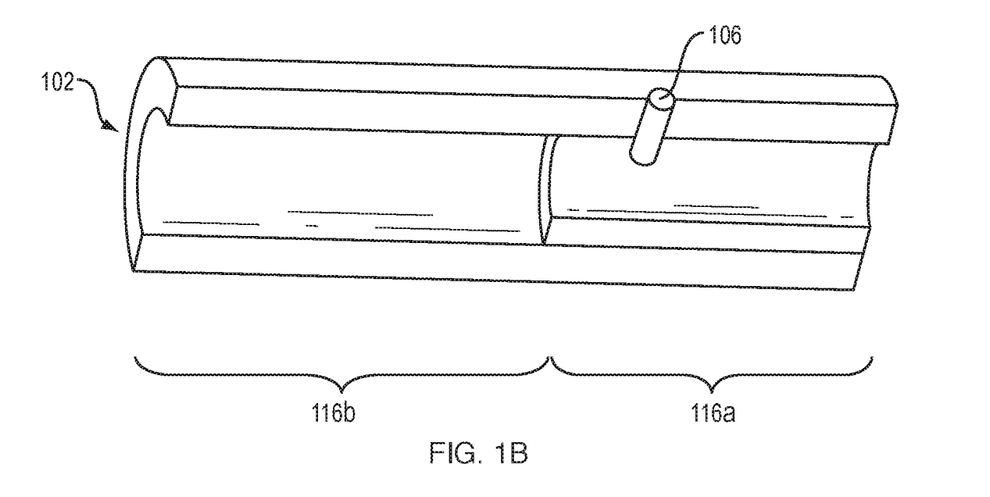
FIGS. 1B-D illustrate details of the embodiment of FIG. 1A.

As shown in FIG. 1B, the cannulation 116 can include a first portion 116a and a second portion 116b. The first portion 116a extends from the proximal end of the housing 102. The second portion 116b is continuous with the first portion 116a and extends from the distal end of the housing 102. The second portion 116b has a diameter smaller than a diameter of the first portion 116a, the diameter being selected to prevent distal movement of the rotatable nut 108. The housing 102 can also include a cam pin 106 secured to the housing 102 and extending traverse to the longitudinal axis within the first portion 116a. The function of the cam pin 106 will be described further below. The nut 108 (FIG. 1A) is disposed within the first portion 116a. The nut carrier 104 (FIG. 1A) is primarily disposed within the second portion 116b but may extend into the first portion 116a.

Figure 1C:
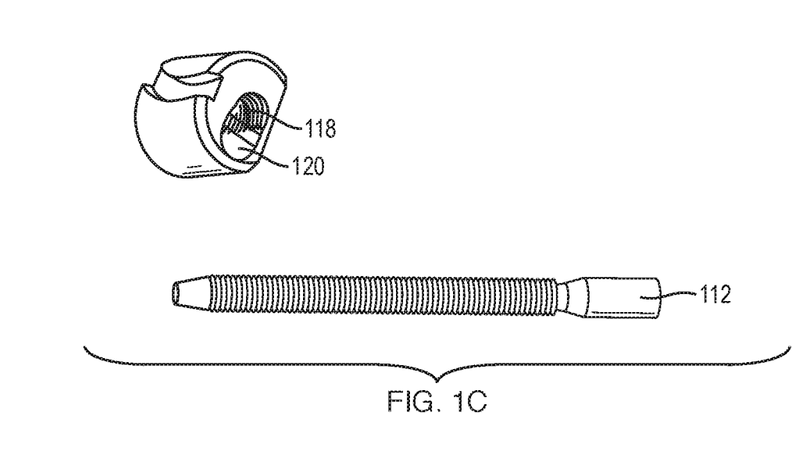

As shown in FIG. 1C, the rotatable nut 108 includes a first, threaded channel 118 formed through a length of the rotatable nut 108 and adapted to threadingly engage the shaft 112. The rotatable nut 108 includes a second, non-threaded channel 120 extending at a selected angle with respect to the first channel 118 and intersecting the first channel 118 at a midpoint of a center line of the threaded shaft 118. The second channel 120 has a diameter greater than a diameter of the shaft 112, the diameter being selected to allow the shaft 112 to slide in the second channel 120.

Figure 1D:
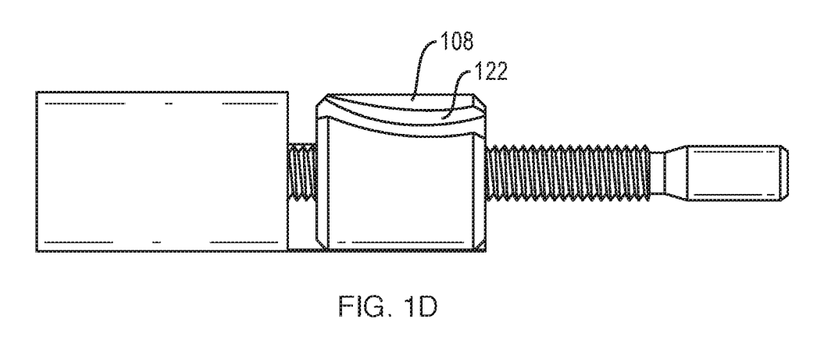

As shown in FIG. 1D, the rotatable nut 108 further includes an arcuate groove 122 formed on an outer surface of the rotatable nut 108 and extending between the proximal and distal ends of the rotatable nut 108. The groove 122 is configured to engage the cam pin 106 (FIG. 1B), as further described below.

Returning now to FIG. 1A, the loading position of the quick release assembly of this disclosure is shown. As shown in FIG. 1A, the first channel 118 (FIG. 1C) of the rotatable nut 108 is oriented such that, when the cam pin 106 engages the groove 122 (FIG. 1D) at about a distal end of the nut 108, the cam pin 106 rotates the rotatable nut 108 into the loading, or unlocked, position, along the direction of unlocking rotation 110. In this position, the second channel 120 (FIG. 1C) of the rotatable nut 108 extends approximately parallel to the longitudinal axis of the housing 102.

Figure 1E:
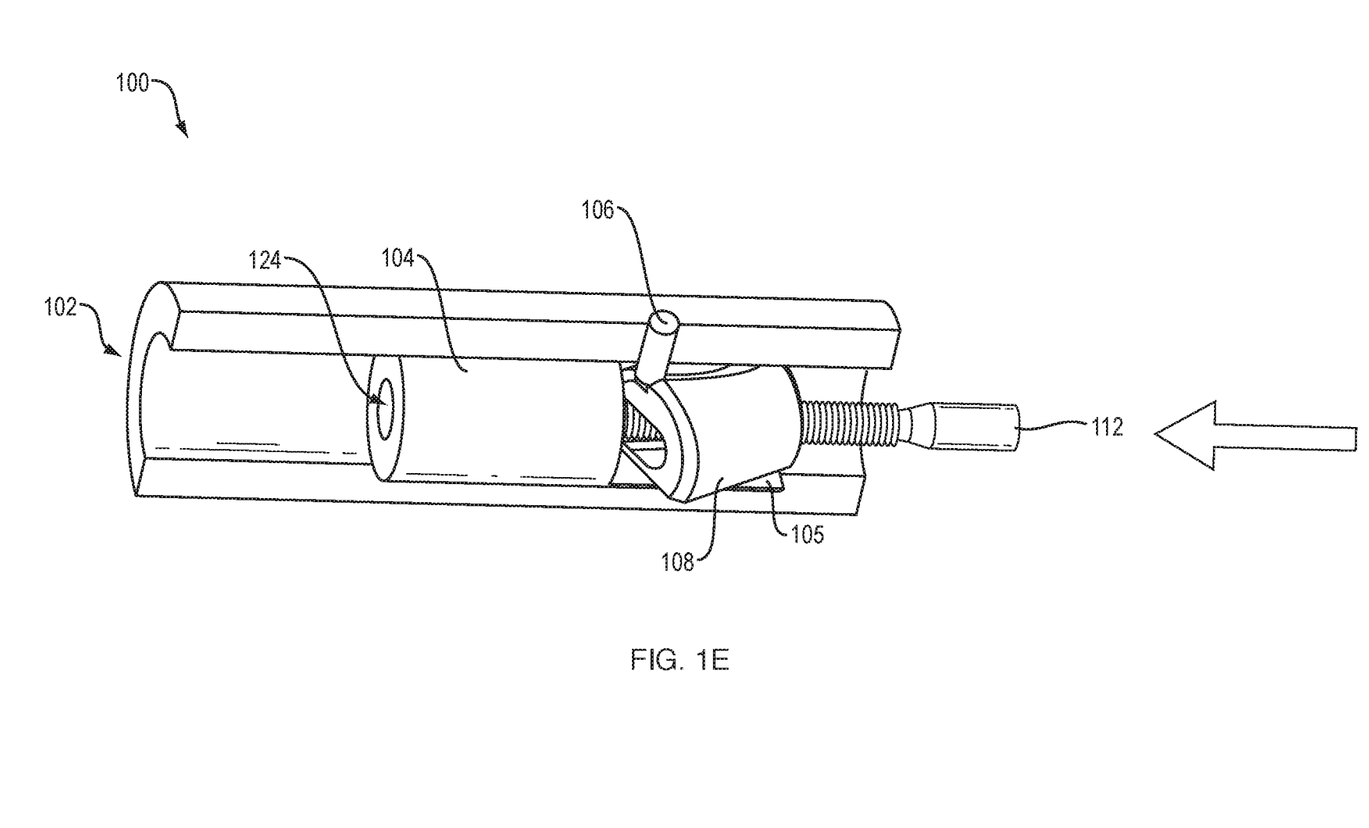
FIG. 1E is a diagram illustrating the transition from the loading to the locking position of the embodiment of FIG. 1A.

As shown in FIG. 1E, the shaft 112 is inserted into the housing 102 through the rotatable nut 108, and partially into the cannulation 124 of the nut carrier 104. It is contemplated by this disclosure that a suture may be attached to the shaft 112 prior to insertion. Once the threaded shaft 112 has found its correct depth within the housing 102, the nut carrier 104 will be drawn back distally within the housing 102, causing the rotatable nut 108 to be rotated by the cam pin 106 into the locked position.

Figure 1F:
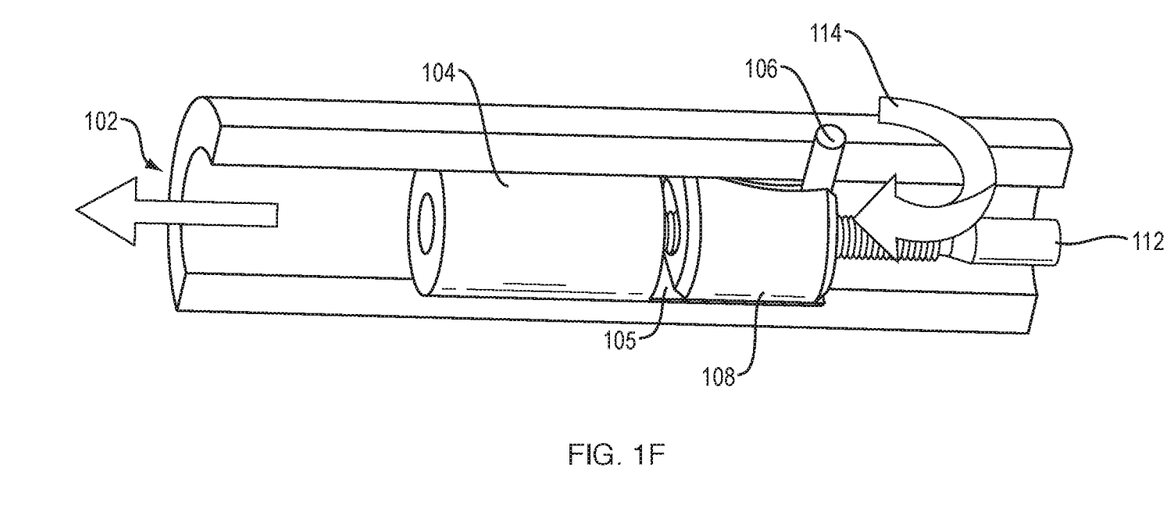
FIG. 1F is a diagram illustrating the locking position of the embodiment of FIG. 1A.

FIG. 1F shows the locked position of the quick release assembly of this disclosure. In FIG. 1F, the rotatable nut 108 is oriented such that, when the cam pin 106 engages the groove 122 (FIG. 1D) at about a proximal end of the rotatable nut 108, the cam pin 106 forces the rotatable nut 108 into the locking position as the nut carrier 104 pulls the shaft 112 into the housing 102. The rotatable nut 108 rotates along a direction of locking rotation 114 to turn into the locking position. The nut carrier 104 is driven back distally along the longitudinal axis of the housing 102, where a reduced housing inside diameter (FIG. 1B) captures and locks the rotatable nut 108 in its locked position. In this position, the first channel 116a (FIG. 1C) extends approximately parallel to the longitudinal axis of the housing 102. The nut carrier 104 is then axially coupled to the rotatable nut 108 by means of the shaft 112, it should be noted that enough clearance inside the housing 102 is required for the nut 108 to rotate into the loading position. At the same time, the clearance inside the housing 102 must also restrict the nut 108 from rotating into a position that would decouple it from the shaft 112.

It should also be noted that insertion of the shaft 112 into the rotatable nut 108 is not inhibited by the second channel 120 when the rotatable nut 108 is in the loading position. As shown in FIG. 1F, distal advancement of the shaft 112. While the rotatable nut 108 is in the loading position engages a distal end of the shaft 112 with the nut carrier 104 and distally advances the nut carrier 104 and rotatable nut 108. The rotatable nut 108 is urged from the loading position to the locking position by the distal advancement of the shaft 112 such that threads of the first channel 118 threadingly engage the threads of the shaft 112.

It is contemplated by this disclosure that the quick disconnect assembly can be configured to allow for the nut to pivot and move along the threaded shaft in small increments without rotating.

While this disclosure has been particularly shown and described with references to example embodiments thereof, it will be understood by those skilled in the art that various changes in form and details may be made therein without departing from the scope of the disclosure encompassed by the appended claims.

The invention claimed is:

1. A quick disconnect assembly, comprising:
   a housing extending along a longitudinal axis between a proximal end and a distal end, the housing further including:
      a cannulation extending between the proximal and distal ends, the cannulation including a first portion extending from the housing proximal end, and a second portion, continuous with the first portion, extending from the housing distal end and having a diameter smaller than a diameter of the first portion; and
      a cam pin secured to the housing and extending transverse to the longitudinal axis within the first portion;
   a nut positioned within the housing cannulation, the nut comprising:
      a first, threaded channel formed through a length of the nut and adapted to threadingly engage a threaded shaft;
      a second, non-threaded channel extending at a selected angle with respect to the first channel and intersecting the first channel, the second channel having a diameter greater than a diameter of the threaded shaft; and
      an arcuate groove formed on an outer surface of the nut and extending between the proximal and distal ends of the nut;
   a nut carrier axially coupled to the nut;
   wherein the first channel of the nut is oriented such that, when the cam pin engages the groove at about a distal end of the nut, the nut is positioned in a loading position where the second channel extends approximately parallel to the longitudinal axis of the housing; and
   wherein the second channel of the nut is oriented such that, when the cam pin engages the groove at about a proximal end of the nut, the nut is positioned in a locking position where the first channel extends approximately parallel to the longitudinal axis of the housing.

2. The quick disconnect assembly of claim 1, further comprising a threaded shaft threadingly engaged with the first channel of the nut.

3. The quick disconnect assembly of claim 2, wherein a clearance inside the housing is selected to allow the nut to rotate into the loading position but to restrict the nut from rotating into a position that would disengage the threaded shaft from the first channel of the nut.

4. The quick disconnect assembly of claim 1, wherein distal advancement of the threaded shaft while the nut is in the loading position engages a distal end of the threaded shaft with the nut carrier and distally advances the nut carrier and nut.

5. The quick disconnect assembly of claim 4, wherein the nut is urged from the loading position to the locking position by the distal advancement of the threaded shaft such that threads of the first channel threadingly engage the threads of the threaded shaft.

6. The quick disconnect assembly of claim 1, wherein insertion of the threaded shaft into the nut is not inhibited by the second channel when the nut is in the loading position.

7. The quick disconnect assembly of claim 1, wherein the housing is tubular.

8. The quick disconnect assembly of claim 1, wherein the diameter of the second portion of the housing cannulation is selected to prevent distal movement of the nut when the nut is in the locking position.

9. The quick disconnect assembly of claim 1, wherein the nut carrier comprises a non-threaded channel.

10. The quick disconnect assembly of claim 9, wherein a diameter of the non-threaded channel of the nut is selected to allow passage of the threaded shaft.

11. A method of connecting a housing and shaft, the method comprising:
   engaging a cam pin secured to a housing with a distal end of a groove formed in the surface of a nut, the nut comprising a first channel in communication with a second channel extending at a selected angle with respect to the first channel and intersecting the first channel, wherein the nut is positioned within a cannulation of the housing such that the second channel of the nut extends approximately parallel to a longitudinal axis of the housing;
   inserting a threaded shaft into the first channel of the nut;
   distally advancing the threaded shaft within the nut until a distal end of the threaded shaft engages with a nut carrier axially coupled to the nut and distally advances the nut carrier and the nut within the cannulation of the housing;
   wherein the distal advancement of the nut within the cannulation of the housing causes the cam pin to move from the distal end of the groove to the proximal end of the groove;
   wherein, when the cam pin engages the proximal end of the groove, the first channel of the nut extends approximately parallel to the longitudinal axis of the housing and the threaded shaft is lockingly engaged with the threaded channel of the nut.

12. The method of claim 11, wherein the cannulation of the housing comprises a first portion and a second portion, a diameter of the second portion being smaller than a diameter of the first portion.

13. The method of claim 12, wherein the diameter of the second portion of the housing cannulation is selected to prevent distal movement of the nut when the threaded shaft is lockingly engaged with the threaded channel of the nut.

* * * * *